(12) United States Patent
Vestre et al.

(10) Patent No.: US 10,196,330 B2
(45) Date of Patent: Feb. 5, 2019

(54) PROCESS FOR DEHYDROAROMATIZATION OF ALKANES WITH IN-SITU HYDROGEN REMOVAL

(71) Applicant: PROTIA AS, Oslo (NO)

(72) Inventors: Per Kristian Vestre, Jar (NO); Christian Kjølseth, Oslo (NO)

(73) Assignee: Protia AS, Oslo (NO)

( * ) Notice: Subject to any disclaimer, the term of this patent is extended or adjusted under 35 U.S.C. 154(b) by 0 days.

(21) Appl. No.: 15/027,918

(22) PCT Filed: Oct. 9, 2014

(86) PCT No.: PCT/EP2014/071697
§ 371 (c)(1),
(2) Date: Apr. 7, 2016

(87) PCT Pub. No.: WO2015/052297
PCT Pub. Date: Apr. 16, 2015

(65) Prior Publication Data
US 2016/0237002 A1 Aug. 18, 2016

(30) Foreign Application Priority Data
Oct. 9, 2013 (GB) .................................. 1317870.2

(51) Int. Cl.
*C07C 2/76* (2006.01)
*B01J 19/24* (2006.01)
(Continued)

(52) U.S. Cl.
CPC .............. *C07C 2/76* (2013.01); *B01J 19/2475* (2013.01); *B01J 29/48* (2013.01); *B01J 29/7876* (2013.01);
(Continued)

(58) Field of Classification Search
None
See application file for complete search history.

(56) References Cited

U.S. PATENT DOCUMENTS

| 5,186,908 A | * | 2/1993 | Nemet-Mavrodin | ..... C07C 2/00 |
| | | | | 422/234 |
| 8,487,152 B2 | | 7/2013 | Coelho Tsou et al. | |

(Continued)

FOREIGN PATENT DOCUMENTS

| WO | 2010115671 A1 | 10/2010 |
| WO | 2010115768 A1 | 10/2010 |

(Continued)

OTHER PUBLICATIONS

International Search Report and Written Opinion issued for International Application No. PCT/EP2014/071697, dated Dec. 23, 2014.

(Continued)

*Primary Examiner* — Philip Y Louie
(74) *Attorney, Agent, or Firm* — Meunier Carlin & Curfman LLC (57) ABSTRACT

A process for conversion of natural gas to aromatic hydrocarbons in a catalytic membrane reactor is described herein. The catalytic membrane reactor comprises a dehydrogenation catalyst and a membrane that can selectively transport hydrogen under high temperature operating conditions such as 600° C. to 800° C. Aromatic hydrocarbons are produced stably for a long time by a process characterized by hydrogen co-feed with the reaction gases to the one end of the to the reaction zone while hydrogen is extracted selectively with use of the membrane as the reactive gas mix passes through the reaction zone.

17 Claims, 5 Drawing Sheets

Schematic drawing of a process of the present invention (51) Int. Cl.
  *B01J 29/48* (2006.01)
  *B01J 29/78* (2006.01)
  *B01J 35/04* (2006.01)
  *B01J 37/30* (2006.01)

(52) U.S. Cl.
  CPC ............ *B01J 35/04* (2013.01); *B01J 37/30* (2013.01); *C07C 2521/04* (2013.01); *C07C 2521/12* (2013.01); *C07C 2523/10* (2013.01); *C07C 2523/22* (2013.01); *C07C 2523/26* (2013.01); *C07C 2523/28* (2013.01); *C07C 2523/30* (2013.01); *C07C 2529/26* (2013.01); *C07C 2529/40* (2013.01); *C07C 2529/46* (2013.01); *C07C 2529/48* (2013.01); *Y02P 20/52* (2015.11)

(56) References Cited

U.S. PATENT DOCUMENTS

| | | |
|---|---|---|
| 2009/0240093 A1 | 9/2009 | Ichikawa et al. |
| 2011/0303550 A1* | 12/2011 | Coelho Tsou ............ C01B 3/26 205/462 |
| 2012/0001122 A1 | 1/2012 | Wattebled et al. |
| 2012/0004482 A1 | 1/2012 | Tsou et al. |
| 2012/0012467 A1* | 1/2012 | Coelho Tsou ............ C01B 3/26 205/338 |
| 2013/0090506 A1 | 4/2013 | Ogawa et al. |
| 2014/0171708 A1* | 6/2014 | Chitta ...................... C07C 2/76 585/417 |

FOREIGN PATENT DOCUMENTS

| | | |
|---|---|---|
| WO | 2011098525 A1 | 8/2011 |
| WO | 2012022569 A1 | 2/2012 |
| WO | 2014085482 A1 | 6/2014 |

OTHER PUBLICATIONS

Coors, et al., "Characterization of composite cermet with 68 wt.% NiO and $BaCe_{0.2}Zr_{0.6}Y_{0.2}O_{3-\delta}$", vol. 376, Issues 1-2, 2011, 50-55.

Illuta, et al., "Methane Nonoxidative Aromatization over Ru—Mo/HZSM-5 in a Membrane Catalytic Reactor", Ind.Eng. Chem. Res. 41, 2002, 2371-2378.

Li, et al., "Design and optimization of catalysts and membrane reactors for the non-oxidative conversion of methane", Chemical Engineering Science 57, 2002, 4595-4604.

Sohrabi, et al., "Thermodynamic Analysis of Nonoxidative Dehydroaromatization of Methane", Chem. Eng. Technol. 35, 2012, 1-9.

Wang, et al., "Dehydrogenation and aromatization of methane under non-oxidizing conditions", Catalysis Letters 21(1), 1993, 35-41.

\* cited by examiner

FIG 1. Schematic drawing of a process of the present invention

FIG 3. Reactor used in Example 1

FIG 4. Thermodynamically equilibrium selectivity
A: As a function of temperature at 1 bara FIG 4B. As a function of pressure at 700°C FIG 5. Benzene formation rate versus time on stream at 700°C, 3000 mL/g h and 3 bara.

PROCESS FOR DEHYDROAROMATIZATION OF ALKANES WITH IN-SITU HYDROGEN REMOVAL

This invention relates to the conversion of natural gas or other alkane feedstock such as bio gas, methane hydrate or methane to aromatic hydrocarbons in a catalytic membrane reactor. In particular, the invention relates to a process in which hydrocarbons such as C1-4 alkanes, mainly methane, are converted to aromatic compounds, such as benzene, utilizing a combination of a dehydrogenation catalyst and hydrogen selective membrane where hydrogen is used as an actual feed to the process. There may also be a recycle of unreacted alkanes and hydrogen in the process. Additionally, in one embodiment, a limited amount of oxygen transport across the membrane into the reaction zone takes place to increase process stability.

BACKGROUND

Natural gas, containing mainly methane, constitutes a large fraction of the world's fossil hydrocarbon resource but is today primarily used as fuel for heating and electricity generation. There is enormous economic potential in developing technologies that convert natural gas to more valuable chemicals. Well established commercial routes for conversion of methane exists e.g. through oxidative reaction paths with synthesis gas (a mixture of CO and $H_2$) as an intermediary product that is then in a second reaction converted to products such as methanol, liquid fuels (by Fisher-Tropsch method) or ammonia (by Haber-Bosch method).

A somewhat less investigated route for natural gas conversion to valuable chemicals is through non-oxidative reactions. Avoiding the oxidation of the natural gas will improve the energy efficiency of the process and thus reduce $CO_2$ emissions while potentially also improving economic return. A promising approach in this context is dehydroaromatization of methane as a method of selective methane conversion directly to aromatic hydrocarbons, mainly benzene, according to the overall reaction formula (I):

$$6CH_4 \rightarrow C_6H_6 + 9H_2 \qquad (I)$$

The groundbreaking work on this approach was published in 1993 by Wang et al, Catal. Lett. 21 35 (1993) and involved a catalyst with molybdenum deposited on HZSM-5 zeolite support with reactions taking place at a temperature of 700° C. Since the publication by Wang et al, many academic groups and commercial companies have been working to improve the process, with some significant progress being made but still with some remaining barriers to large scale commercial deployment.

Non-oxidative dehydroaromatization of methane to benzene is thermodynamically limited, leading to two significant technological obstacles to scale-up and commercialization:

1) The fact that the equilibrium conversion of methane at typical reaction temperature 700° C. and pressure 1 bar is thermodynamically limited to about 12% aromatic product (M. Sohrabi et al., Chem. Eng. Technol. 2012, 35, No. 00, 1-9), with experimental conversion often reported to be slightly less at around 8-11%; and 2) The formation of several forms of carbon deposits in the catalyst bed, including polyaromatic hydrocarbons, leading to rapid deactivation of the catalyst and very short catalyst lifetime.

Several groups have proposed the use of hydrogen selective membranes for thermodynamic equilibrium shift as a solution to overcome obstacle 1) noted above. For example, Li et al. Chemical Engineering Science 57 (2002) 4595-4604 have laid out numerical models to support such an approach. Illuta et al. in Ind. Eng. Chem. Res. 2002, 41, 231-2378 have demonstrated use of a hydrogen permeable Pd-membrane to shift the equilibrium of the methane dehydroaromatization process. One problem with Pd-membranes is that they promote the undesirable side reactions 2) towards coke formation. WO2010/115671 describes a method to electrochemically remove hydrogen from a reaction mixture using an electrochemical membrane electrode assembly. In principle, this works similar to the hydrogen permeable membrane but using an applied bias instead of a chemical potential gradient through a partial pressure difference in $pH_2$. Such a process will be subject to significant formation of polyaromatic hydrocarbons and coke.

The present inventors have proposed the use of a lanthanum tungstate based mixed metal oxide membrane as set out in WO2011/098525 to overcome the limitations of pre-existing membranes. However, the equilibrium shift over a membrane in itself does not solve the fundamental problem of coke formation and deactivation of the catalyst.

Thus whilst removal of hydrogen brings the equilibrium over towards the right hand side of the equation (I) above, it will be appreciated that the dehydrogenation catalyst employed also causes conversion of methane through to carbon itself and that conversion process is also encouraged by hydrogen removal.

Another approach to obstacle 1) above is to accept a low/moderate single pass conversion and focus the design of the process towards an efficient recycle of unreacted alkanes back into the reactor. This requires hydrogen removal from the recycle gas outside of the reaction zone. Coelho et al. describes such a process in WO2010/115768 (U.S. Pat. No. 8,487,152 B2), where hydrogen is electrochemically removed from the product stream outside of the reaction zone and then unreacted alkanes are recycled back into the reactor. The removal of hydrogen in an external gas loop does not in itself solve the problem of coke formation with subsequent deactivation of catalyst but the toleration of low yields helps reduce its formation. A process scheme that has been proposed by several groups to overcome obstacle 2) above is described in for example in US2009/0240093. The idea is to add an amount of hydrogen, water and/or $CO_2$ to the feed gas for the purpose of suppressing coke formation and increase the catalyst time on stream. A somewhat different process proposed by US 2013/0090506 describes an alternative process where hydrogen pulses are used in the feed process.

The drawback of such a process is that co-feeding with hydrogen moves the equilibrium to the left and hence reduces the formation of aromatic hydrocarbons.

Another process scheme to overcome obstacle 2) above is to let the catalyst deactivate and have a continuous system for moving the catalyst between a compartment for dehydroaromatization and compartment for catalyst regeneration. One variant of this approach has been commercialized by UOP under the Cyclar trademark and is described for example by Fukanaga in Chemical Engineering (Tokyo), Vol. 44; No. 4; page 283-287(1999).

Another variant for continuous catalyst regeneration is a duel-zone fluidized bed, such as the design described by Scheinder et al in WO2012/022569. A drawback of continues movement of catalyst between different compartments is increased complexity and cost of the entire system.

Thus, there is a need to develop a new alkane dehydroaromatization process that represents an acceptable compromise between high yield conversion of light alkanes to aromatics and long catalyst life time.

The present inventors have realised that the dehydroaromatization of alkanes such as methane in the presence of a dehydrogenation catalyst can be improved by the addition of hydrogen as a feed to the reactor in combination with removal of hydrogen from the reactor and optionally in combination with a recycle of hydrogen and/or unreacted starting material. Furthermore, process stability might be improved by allowing a limited amount of oxygen transport through the membrane into the reactor zone.

By feeding hydrogen at the start of the process, the initial equilibrium in the reaction in scheme 1 above is moved to the left thus avoiding initial coke formation and maximising catalyst life. Thereafter, by removing hydrogen within the reactor, the thermodynamic equilibrium can be at least maintained or optionally subsequently shifted to the product side as the reactants pass through the reactor. This process allows a dynamic control over the equilibria within the process thus maximising yields whilst minimizing coking of the catalyst.

Thus, the reaction gas mixture, temperature, pressure etc may change as the reaction gases (and product gases) move through the reactor from the inlet to the outlet. A key benefit of the invention is that the combination of co-feed with hydrogen and use of the hydrogen membrane allows the operator to optimize the partial pressure of hydrogen dynamically throughout the length of the reactor, so as to maximize selectivity and minimize coke formation. An added benefit is the economical integration of a recycle loop for unreacted gases with no need for external hydrogen separation from the unreacted gas mix as the reactor system itself has in-situ hydrogen removal. Another added benefit is an increase in process stability due to a controlled oxygen transport into the reactor zone through the membrane, which decreases the coke formation.

SUMMARY OF THE INVENTION

Thus, viewed from one aspect the invention provides a process for the preparation of an aromatic hydrocarbon, such as benzene, in a catalytic membrane reactor comprising a reactor inlet, a dehydrogenation catalyst and a reactor outlet in a first zone arranged so that a feed to the reactor via the inlet must contact the dehydrogenation catalyst before passing to the reactor outlet;

and a hydrogen transport membrane separating said first zone from a second zone; said process comprising:

(I) feeding through said reactor inlet a feed comprising hydrogen and at least one C1-4 alkane so that the alkane and hydrogen contact said dehydrogenation catalyst in said first zone;

(II) operating said reactor at a temperature and pressure sufficient to allow dehydrogenation of said alkane and formation of said aromatic hydrocarbon and hydrogen;

(III) allowing hydrogen to selectively pass through the hydrogen transport membrane into said second zone;

(IV) recovering through the reactor outlet in the first zone, said aromatic hydrocarbon along with any unreacted C1-4 alkane and any hydrogen not extracted through the hydrogen transport membrane;

(V) separating the aromatic hydrocarbon from the hydrogen and any unreacted C1-4 alkane; and optionally (VI) recycling at least a part of said hydrogen and/or any unreacted C1-4 alkane to the feed.

Viewed from another aspect the invention provides a process in which step (VI) is present, especially where both alkane and hydrogen are recycled.

It will be appreciated that hydrogen transfer through said membrane may take place in the form of protons.

Further, in one embodiment a fraction of the transported species in the membrane takes place in the form of oxygen ions from second zone to first zone. In this embodiment, the second zone is supplied with an oxygen containing species as a source of oxygen.

Viewed from another aspect the invention provides a process for the preparation of an aromatic hydrocarbon, such as benzene, in a catalytic membrane reactor comprising a reactor inlet, a dehydrogenation catalyst and a reactor outlet in a first zone arranged so that a feed to the reactor via the inlet must contact the dehydrogenation catalyst before passing to the reactor outlet;

and a hydrogen transport membrane separating said first zone from a second zone; said process comprising:

(I) feeding through said reactor inlet a feed comprising hydrogen and at least one C1-4 alkane so that the alkane and hydrogen contact said dehydrogenation catalyst in said first zone;

(II) operating said reactor at a temperature and pressure sufficient to allow dehydrogenation of said alkane and formation of said aromatic hydrocarbon and hydrogen;

(III) allowing hydrogen to selectively pass through the hydrogen transport membrane into said second zone;

(IV) removing hydrogen from said second zone in order to establish a concentration gradient for hydrogen transport between said first and second zones;

(V) recovering through the reactor outlet in the first zone, said aromatic hydrocarbon along with any unreacted C1-4 alkane and any hydrogen not extracted through the hydrogen transport membrane;

(VI) separating the aromatic hydrocarbon from the hydrogen and any unreacted C1-4 alkane; and optionally (VII) recycling at least a part of said hydrogen and/or any unreacted C1-4 alkane to the feed.

In a further preferred embodiment, oxygen passes though the hydrogen transport membrane from said second zone in to said first zone, e.g. during step (III). In this embodiment, the second zone is supplied with an oxygen containing gas species as a source of oxygen. Ideally, that oxygen source reacts with hydrogen as a way of removing hydrogen from the second zone as explained in step (IV).

DETAILED DESCRIPTION OF INVENTION

This invention relates to a process for the dehydrogenation of alkanes to form aromatic hydrocarbons. The invention relies on the use of hydrogen as a feed to a process for dehydroaromatisation of alkanes and the removal of hydrogen from the reactor during the actual dehydrogenation process.

The present invention therefore involves controlling the partial pressure of hydrogen ($pH_2$) fed into a catalytic membrane reactor and selectively removing hydrogen from the reactor along the flow-path of the reaction gases in the reaction zone to shift the thermodynamic equilibrium in the reaction zone.

In a further embodiment, the present invention also involves controlling oxygen transport through the membrane into the reaction zone (also called the first zone herein). By allowing oxygen transport into the reaction zone we can decrease the formation of polyaromatic hydrocarbons and coke.

The present invention relates to a process for dehydroaromatization of alkanes to form aromatic hydrocarbons. The most common alkane starting material of use in this invention is natural gas, methane hydrate, methane or biogas. In general however, the process can be carried out on C1-4 alkane feedstocks or mixtures of such alkanes such as ethane or methane. It is preferred if methane is the most abundant component of the alkane starting material. Thus methane preferably forms at least 50 wt % of the starting material relative to the total content of alkanes fed to the reactor of the invention.

Ideally, methane forms at least 60 wt %, such as at least 70 wt % of the alkanes fed to the reactor, such as at least 80 wt %. Alternatively viewed, methane forms at least 60 vol %, such as at least 70 vol % of the alkanes fed to the reactor, such as at least 80 vol %.

The product aromatic hydrocarbon can be benzene, toluene, xylene, naphthalene or an other mono or bicyclic aromatic hydrocarbon. The product should not be a polycyclic aromatic hydrocarbon having three rings or more as these compounds act as poisons for the dehydrogenation catalyst. Typically, the reaction of the invention produces mostly benzene. Benzene preferably forms at least 50 wt % or 50 vol % therefore of the aromatic compounds formed in the process of the invention. Alternatively viewed, benzene forms at least 60 vol %, such as at least 70 vol % of the aromatic compounds formed in the reactor, such as at least 80 vol %.

The actual yield of aromatic compounds can vary depending on the nature of the equilibrium in the reaction, and will among other factors depend on operating temperature and pressure. In a dehydrogenation reactor to convert methane to benzene without a membrane to remove hydrogen, equilibrium conversion of methane at typical reaction temperature 700° C. and pressure 1 bar is thermodynamically limited to about 12% aromatic product (M. Sohrabi et al., Chem. Eng. Technol. 2012, 35, No. 00, 1-9). In the present invention that includes both a co-feed of hydrogen and a hydrogen transport membrane for in-situ hydrogen removal, there is no absolute thermodynamic limit for the reaction, but yields of aromatics between 1 and 35% are possible, depending on operating conditions such as temperature, pressure, flowrates and balance of plant integration. The hydrogen transport membrane may additionally allow a portion of oxygen to cross the membrane from second zone to first zone to feed the reactor in-situ with oxygen. The presence of this small amount of in situ oxygen avoids formation of polyaromatic hydrocarbons and coke during the reduction of the alkanes.

The process of the invention can therefore be summarised by the following reaction formula (1)

$$6CH_4 \leftrightarrow C_6H_6 + 9H_2 \quad (1)$$

In more general terms, the process involves:

$$A \leftrightarrow B + H_2 \quad (IV)$$

wherein A comprises one or more C1-C4 alkanes (such as methane)

B comprises one or more mono or bicyclic aromatic hydrocarbons (such as benzene).

It is important to note that the thermodynamics for this reaction do not favour complete conversion from feed (alkanes) to desired product (aromatics). A typical yield for much of the development work by various groups for this process is around 7 to 14% (on a carbon atom basis) depending on operating conditions and choice of catalyst. At that higher end of the above yield range, however, catalyst deactivation becomes a significant problem and only a modest catalyst lifetime of less than 24 hours are typically reported for yields in the high end of the above range.

Note that hydrogen is produced by this reaction so the addition of hydrogen to the feed as claimed herein is counter-intuitive. The addition of hydrogen in the feed with the alkane reactant has the effect of forcing the equilibrium illustrated above towards the starting material side and hence would apparently reduce the yield of the target aromatic compounds.

The present invention however also seeks to avoid a reaction in which alkanes convert to carbonaceous deposits such as coke. This reaction generally follows the formula:

$$A \leftrightarrow Coke + H_2 \quad (V)$$

It follows from the equation (V) above that lower partial pressures of hydrogen in the reactor will favour increasing carbon deposits. The carbonaceous deposits which form become bound to the dehydrogenation catalyst causing its deactivation. This process can lead to very short catalyst lifetimes. When running a process to achieve maximum yield and hence most aggressive dehydrogenation, coking is a problem. The present inventors have realised that the addition of hydrogen with the feed of alkane reduces the incidence of coking and hence increases catalyst lifetime.

Several parameters determine the equilibrium of the reactions above, such as temperature and pressure and also the co-feeding of $H_2$. The parameters are interlinked.

Higher temperatures tend to lead to more coking and hence will require a higher mol % hydrogen co-feed to slow down coking as compared to reactions carried out at lower temperatures.

Higher pressures however works the other way around, reducing coking and hence requiring a lower mol % hydrogen co-feed to slow coking.

The amount of hydrogen fed to the reactor may vary depending on the pressure and temperature conditions employed within the reactor. In general terms however, the hydrogen feed should represent 3 to 35 vol % of the feed to the reactor, with the low end of the range suitable for lower temperatures and higher pressures and the higher end of the range suitable for higher temperatures and lower pressures. Suitable ranges may therefore include 7 to 30 vol % hydrogen in the gas feed, such as 10 to 25 vol %. A most preferred range may be 10 to 20 vol % hydrogen in the gas feed.

We have also found that an additional parameter that determines the stability of the process is the concentration of oxygen in the first zone. In general, it is evident that most oxide proton conductors have an ionic transport number of oxygen lower than that of protons, e.g. t(oxygen)=0.1 and t(proton)=0.9, where t(oxygen)+t(proton)=1. Further t(oxygen) usually increases with increasing temperature. Introduction of oxygen into the reaction chamber from the permeate sweep gas can lead to the following reaction:

$$O + 2H \leftrightarrow H2O \quad (VI)$$

which further leads to a reaction with carbon:

$$C + H2O \leftrightarrow CO + H2 \quad (VII)$$

Hence the presence of a small amount of oxygen in the reactor zone can help reduce coke formation. It is preferred if the t(oxygen) is between 0.001 and 0.5 such as 0.01 to 0.2 most preferably between 0.05 to 0.1. It is generally not preferred to add oxygen into the actual feed stream itself. Thermodynamically, any oxygen fed with the alkane type feed will form CO through pyrolysis. This will most likely happen spontaneously before the feed gas even enters the reaction chamber. CO will act as an inert dilution gas.

Instead, in this invention we have found that the membranes we use can selectively allow oxygen through the membrane from the second zone to the first zone. By supplying therefore an oxygen containing species to the second zone, we can allow a small portion of oxygen to transfer across into the first zone.

In general, a lower degree of hydration of the membrane will increase the oxygen transport across the membrane. An increase in reaction temperature will also tend to increase oxygen transport.

Hydrogen Transport Membrane

It is a critical feature of the invention that the reactor is provided with a hydrogen transport membrane which selectively allows hydrogen to leave the main dehydrogenation and aromatisation zone of the reactor through the membrane but does not allow the starting material alkanes and product to pass through. The membrane separates the first reaction zone in which the dehydrogenation and aromatisation takes place (i.e. in which the feed and dehydrogenation catalyst come together) from the second zone which will contain hydrogen which passes through the membrane and any means desired to remove that hydrogen.

In one embodiment, the hydrogen transport membrane has some oxygen ion transport properties as well. If the permeate sweep comprises an oxygen containing gas, there will be a gradient to allow oxygen to transport from the permeate side to the reactor chamber, i.e. across the membrane. A small amount of oxygen in the reactor chamber is favourable to reduce coke formation. Such a oxygen containing material can be water (steam).

Thus, the hydrogen transport membrane must be of a material that can selectively transport hydrogen, preferably in ionic form as protons. It is preferred if the membrane material is chemically inert and stable at temperatures between 500° C. and 1000° C. in atmospheres containing gases such as alkanes, hydrogen and $CO_2$. The membrane material should not promote carbon deposits in the reactor, which typically means that the material should have very low tendency towards carbon uptake and also should have a surface that does not catalytically promote activation of alkanes, in particular methane.

One group of materials that can meet these requirement is some mixed metal oxides, and it is preferred if the membrane material used in the hydrogen transport membrane comprises a mixed metal oxide. Ideally, the transport membrane will possess a proton conductivity of at least $1 \times 10^{-3}$ S/cm. The proton conductivity of the membrane of the invention is preferably at least $1.5 \times 10^{-3}$ S/cm, especially at least $2 \times 10^{-3}$ S/cm. Further, ideally the membrane of the invention should an oxygen transport number of 0.001 to 0.5, such as 0.01 to 0.2, preferably between 0.05 and 0.1.

A range of mixed metal oxides may be suitable, including acceptor doped perovskites (such as Y-doped $BaZrO_3$, Yb-doped $SrCeO_3$, Y—$BaCeO_3$ and Sr-doped $LaCrO_3$), rear earth tungstates and acceptor doped lanthanum niobates.

The present inventors have previously outlined such a membrane in WO2011/098525 according to the formula (II):

$$Ln_aW_bO_{12-y} \qquad (II)$$

wherein Ln is Y or an element numbered 57 to 71; the molar ratio of a:b is 4.8 to 6, preferably 5.3 to 6; and y is a number such that formula (I) is uncharged, e.g. $0 \leq y \leq 1.8$.

Figure 1:
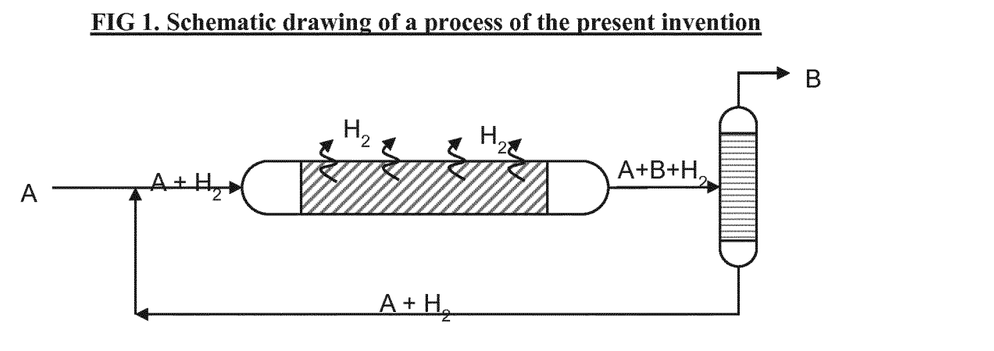
Figure 2:
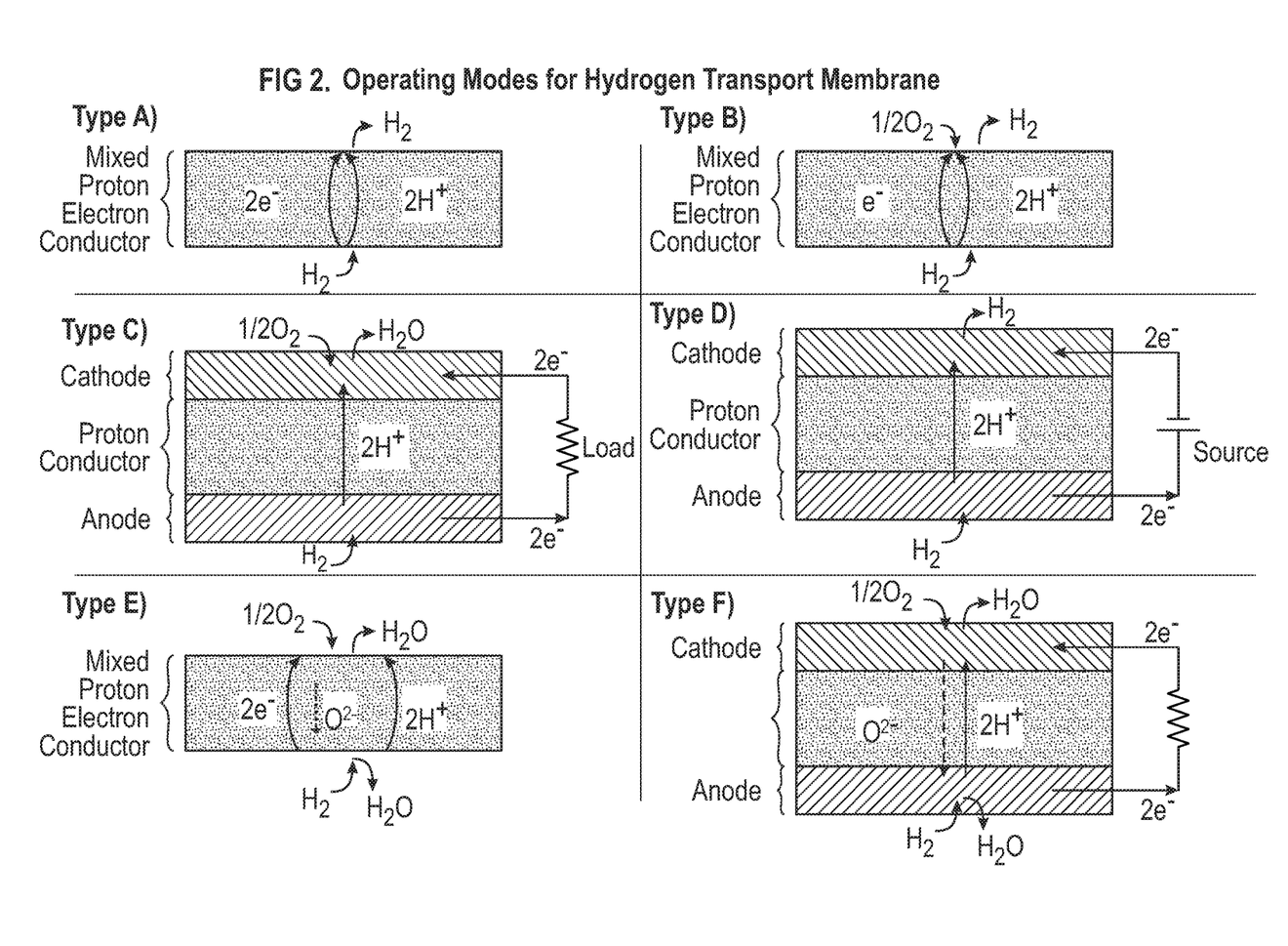
FIG. 2 illustrates examples of the different types of solid oxide membrane assemblies for the hydrogen transport membrane used in the present invention.
Figure 3:
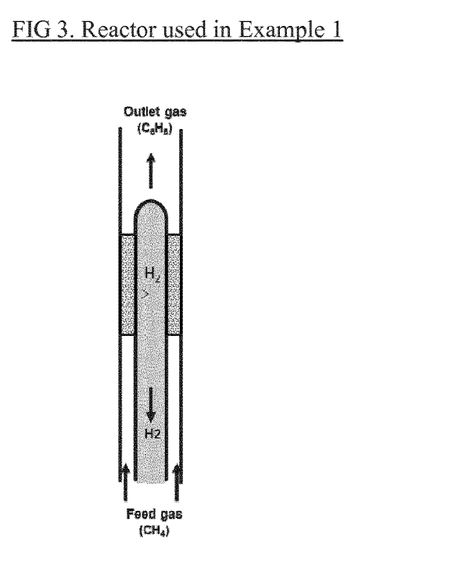
FIG. 3 is a drawing of the catalytic membrane reactor used in Example 1. Fed gas passes up the outside walls of the membrane and through catalyst bed (5). Hydrogen is transported across membrane (2) into the central tube of the reactor where it is removed. Outlet gases are those that pass through catalyst bed (5).

Laboratory experiments by the present inventors have shown that membranes comprising at least one phase of the above material may be operated in accordance with FIG. 2, type A (reducing permeate side) and FIG. 2, type B (oxidative permeate side).

An alternative operating modus to facilitate hydrogen transport across the membrane is to apply a voltage over an electrode-electrolyte-electrode assembly as illustrated in FIG. 2 type C, or as a further alternative, to operate the membrane as a hybrid fuel cell and extract electric power as illustrated in FIG. 2 type D. Also in these events, the electrolyte of the membrane is preferably a mixed metal oxide or mixture thereof. Other preferred membrane materials therefore include pervoskites according to the general formula (III)

$$AB_{1-q}B'_qO_{3-z} \qquad (III)$$

wherein A=La, Ba, Sr or Ca; B=Ce, Zr, Ti, In, Tb, Th or Cr and B'=Y, Yb, Gd, Pr, Sc, Fe, Eu or Sm: z is a number sufficient to neutralize the charge; and $0.01 \leq q \leq 0.5$.

In general, operation of the transport membrane can be carried out using techniques known in the art. It will be appreciated that electrodes may be added to operate the membrane, in which case attention must be given to make sure that the electrode exposed to the first zone of the reactor should have following characteristics:

Electronic percolation

Catalytic activity towards hydrogen dissociation

Porous microstructure to allow gas diffusion of $H_2$ to triple phase boundaries and avoid concentration polarization due to accumulation of larger hydrocarbon molecules Resistant towards the promotion of coke of all kinds (including the formation of polyaromatics, "whisker" coke and other forms of carbon deposits)

Chemical compatibility with the electrolyte

Chemical compatibility with catalyst under reactor operation

The electrode can be a single phase or composite with multiple phases. Some potential candidate materials include the following groups:

Metals/metal alloys (such as Ag, Cu and Pd alloys)

Mixed metal oxides (such as acceptor doped LaCrO3)

Carbides (such as WC)

The second electrode not exposed to the first zone in the catalytic membrane reactor may be selected from a wider range of materials known to those skilled in the art of making solid oxide fuel cells (SOFC).

The hydrogen transport membrane assemblies can be fabricated with such techniques generally known to those skilled in the art of making solid oxide fuel cells and inorganic gas separation membranes.

Support

It may be necessary to use a support to carry the membrane or catalyst described in more detail below. In some embodiments, the membrane of the invention is self supporting however, it is within the scope of the invention to use a support. The support should be inert, porous and capable of withstanding the conditions within the reactor.

The following are important properties for the support:

Porous

Chemically compatible with the membrane—does not react to form a secondary insulating phase;

Mechanically compatible with the membrane—thermal expansion coefficient should preferably match that of the membrane.

Typically the support will be an inert metal oxide such as an alkali metal oxide or silica or alumina. Such supports are well known in this field. In general, the particle size in the support should be greater than the particle size in the membrane, e.g. at least 200 nm higher. Supports may be 2-300 µm to 1 mm or more in thickness.

The design of the support material depends on the design of the whole reactor. Typically the membrane, and hence any support, will be planar or tubular. The term tubular may be used herein to designate a membrane that is a hollow cylinder with two open ends, or alternatively it may be a plurality of smaller channels forming a "honeycomb structure" or it can take the shape of a "test tube", i.e. a cylinder with hemispherical end portion but open at the other end.

In a tubular embodiment, porous support tubes can be extruded. Both thermoplastic and water based extrusion processes can be used. The support is then heat treated to yield the desired mechanical strength. In a planar embodiment the support material can be tape cast, also followed by heat treatment to yield the desired mechanical strength. In a tape casting process, a slurry of the material is typically spread evenly onto a flat horizontal surface by means of a doctor blade. After drying, the thin, film formed can be removed, cut to the desired shape and fired.

To manufacture a support structure either as a planar support or as a tube, an ink of the desired support material can be produced either using water as a solvent or an organic solvent, optionally as well as stabilizing agents. To have controlled porosity, a pore filler material is often used, e.g. carbon black. The ink can then be tape cast or extruded. The support is subsequently fired to a desired firing temperature, such as 600 to 1500° C. to yield mechanical robust supports with a desired porosity.

In a complex design embodiment, the porous support tubes can be prepared by gel casting. A mould is prepared of the desired structure. A solution of the desired material is then prepared and poured into the mould. After the solution is gelified the mould is removed. The support is subsequently fired to a desired firing temperature, such as 600 to 1500° C. to burn out the organic residue and to yield mechanically robust supports with a desired porosity.

In the simplest embodiment, the membrane is self supported. In one embodiment however, the invention is multilayered and is formed from a layer of the hydrogen transport material, a layer of the dehydrogenation catalyst and optionally a support layer. In use, it will be clear that the membrane must be oriented such that the dehydrogenation catalyst layer contacts the fed gases first to allow the dehydrogenation reaction to take place.

The membrane will typically be formed using a layer which may have a thickness of 1 to 500 micrometers, such as 10 to 150 micrometers. Membranes having thickness in the lower end of the range will require a structural support, while membranes with thickness in the higher end of the indicated thickness range may typically be "self-supported".

The amount of catalyst in the membrane, i.e. the thickness of the catalyst layer may vary between 10 µm to 10 mm, e.g. depending choice of materials and reactor design.

Alternatively, the membrane can be formed simply from the mixed metal oxide and optional support with the dehydrogenation catalyst forming, for example, a matrix within the reactor which the feed passes through. The catalyst may be provided therefore as a particulate bed.

Several thin film techniques can be used to deposit membranes. These include, for example:
Screen printing;
Chemical vapour deposition techniques (CVD);
Spray deposition methods—e.g. ultrasonic spray deposition (USD);
Electrophoretic deposition;
Spin and dip coating;
Slurry coating; and
Impregnation.

Screen printing, spray deposition and spin/dip coating are preferred techniques. Screen printing is easy to upscale and can readily achieve thicknesses down to 10 µm.

The membrane will preferably be formed as a planar membrane or tubular membrane, especially a tubular membrane.

In a planar embodiment the membrane is preferably deposited on a porous support using a screen printing technique.

The process of the invention requires that the starting material and hydrogen are fed in the reactor. The temperature of the feed is such that the materials are fed as gases but typically, the feed will be heated to have the same temperature as the reactor.

The dehydroaromatization process within the reactor is normally operated at high temperatures of 500° C. to 1000° C., preferably 600° C. to 800° C. The pressure within the reactor may range from 0.5 to 50 bar, preferably 1 bar to 10 bar.

There needs to be a flow from the inlet to the outlet within the reactor. Feedstock gas flow, measured as GHSV (gas hourly space velocity) is normally in the range 500-30,000 mL/gh, more preferred in the range 1000-10,000 mL/gh.

The process is preferably carried out in a non-oxidative environment so there should be no oxygen present in the fed. Note however that small amounts of $H_2O$, $CO$, $CO_2$ as well as other oxygen containing gases may be present in small quantities, e.g. as impurities in a natural gas feed or as may be necessary to hydrate the hydrogen transport membrane. If any such gases are present these are preferably present in amounts of less than 5% by volume, preferably less than 2% by volume, especially less than 1% by vol. The term non oxidative can be used herein therefore to imply the presence of less than 5 vol % of any oxygen containing gases in the feed. Ideally, the only gases fed to the reactor are hydrogen and the alkanes.

In one embodiment however, some oxygen can transport from the permeate side of the membrane to the reactor chamber. It is important to differentiate between this in-situ introduced oxygen and any oxygen in the actual feed stream. Ideally, there is no oxygen in the feed stream and any oxygen present in the reaction chamber derives from transport across the membrane from the second zone. The oxygen introduced in-situ may react with polyaromatic hydrocarbons or coke to decrease the deactivation of the catalyst.

Hydrogen is generated during the dehydrogenation reaction and the amount of hydrogen removed from the reactor via the transport membrane can be manipulated depending on how the user wants the process to be run.

It may be therefore that the operator wants to remove all the hydrogen generated during the actual dehydrogenation reaction to maintain at the outlet the same hydrogen concentration that was present at the inlet. He may however want to remove more hydrogen than is generated by the actual dehydrogenation reaction (i.e. the outlet hydrogen concentration will be lower than the concentration at the inlet) forcing the equilibrium to the right. Alternatively, less hydrogen can be removed than is generate during dehydrogenation such that the outlet hydrogen concentration is higher than that at the inlet.

The optimal dynamic hydrogen content in the reaction gas will depend on the properties of the catalyst and the operating conditions, including temperature, pressure and flow rate. Different catalysts may be used in different parts of the first reactor zone and different operating conditions may also be used in different parts of the first reactor zone. For example the gas inlet temperature may be higher than the gas outlet temperature. In such a case the operator may want to adjust hydrogen co-feed and hydrogen extraction with use of hydrogen transport membrane to optimize for a particular dynamic situation found in the reactor.

The process may be governed by the relative likelihood of coke formation as the reaction equilibrium is changed by the hydrogen level within the reactor. The inventors perceive that by minimising coke formation, the process of invention, which is preferably continuous can be run over and over before any catalyst regeneration is needed. Whilst therefore the overall yield of a single pass through the reactor may be lower than can be achieved without hydrogen feed, the process of the invention enables multiple passes of the starting material without catalyst deactivation leading to an overall higher yield relative to the cost of deactivation.

By removing hydrogen from the reactor however, we still allow an acceptable yield to be obtained. Without hydrogen removal, as the process proceeds hydrogen concentration builds up reducing the aromatic compound yield.

In one embodiment, it is preferred if the ratio of hydrogen to alkanes in the feed is at least $0.25 \times S_{max}$ on a molar basis. Herein $S_{max}$ is defined to be the hydrogen to alkane ratio giving the highest theoretically calculated thermodynamic equilibrium selectivity for benzene relative to the selectivity for all other hydrocarbon products under the relevant operating temperature and pressures. Example calculations indicating the maximum thermodynamic equilibrium selectivity for benzene relative to the selectivity for other hydrocarbon products under some examples of relevant operating temperature and pressures are set out in FIG. 5.

In one embodiment of the invention the process may require that the ratio of hydrogen to alkanes on a molar basis is higher at the feed side then at the product side of the catalytic membrane reactor or that the ratio of hydrogen to alkanes on a molar basis is constant along the flow path of the first zone of the catalytic membrane reactor.

Thus, in one embodiment the process is operated as follows:

1. Constant $pH_2$: co-feed $H_2$, then remove all produced hydrogen to maintain co-feed level. Inlet $pH_2$=outlet $pH_2$. Preferred co-feed (and outlet) may be in 10% to 20% vol range, dependent on pressure and temperature.

2. Decreasing $pH_2$: co-feed high $pH_2$ to promote C2 selectivity in low end of reactor. Remove more than produced hydrogen so that $pH_2$ is declining through reactor. Preferred co-feed may be in 15% to 30% range. Preferred outlet hydrogen concentration may be in 10% to 20% vol range.

3. Increasing $pH_2$: co-feed is moderate to place emphasis on conversion, produced $H_2$ is only partially removed. Co-feed in 5-15% range. Outlet $H_2$ in 15% to 20% vol range.

The electrochemical driving force for the hydrogen transport across the hydrogen membrane is preferably the result of an external voltage being applied to the membrane or is the result of a difference in the partial pressure of hydrogen on the two sides of the membrane.

Alternatively, the partial pressure of hydrogen at the permeate side of the membrane (the second zone) is maintained at a low level by sweeping with an oxygen containing gas to convert at least some of the permeating hydrogen to water on the permeate side of the membrane. This creates a gradient for hydrogen transport.

Dehydrogenation Catalyst

The reactor used in the present process requires a dehydrogenation catalyst. The catalyst catalyses the conversion of the alkane to the aromatic hydrocarbon, e.g. methane to benzene. Any dehydrogenation catalyst capable of achieving the desired process can be used. Preferably however, a bi-functional catalyst comprising one or more metals deposited on a shape selective catalyst is used. That is typically therefore a zeolite catalyst.

The dehydrogenation catalyst may be integrated in the catalytic membrane reactor as a packed fixed bed, as a fluidized bed, by deposition on the membrane wall, or in other way.

The dehydrogenation catalyst is preferably a porous catalyst but it should ideally have some electron and proton conductivity as these species may need to be transported through the catalyst on the membrane.

Suitable catalysts include oxides of the first row of transition metals such as Ni, Fe, Pt, Ag, Pd and their alloys. These can be supported on alkali metal oxides. Suitable examples are $CrO_2$, $MoO_3$ and $V_2O_5$.

Some perovskite compounds may be suitable as catalysts such as those of formula $AB_{1-q}B'_qO_3$, where A=Ca, Sr or Ba; B=Ce, Tb, or Pr; B'=Ti, V, Cr, Mn, Fe, Co, Ni, or Cu or combinations thereof; and $0.02<q<0.5$.

Preferably, however, the catalyst is a zeolite. Preferred zeolites are those having the structure, MWW, CHA, MFI, TUN, TON, IMF and MTW, e.g. CHA, MFI, TON and MTW. Specifically preferred structures are MCM-22 SAPO-34, SAPO-11, SAPO-44, ZSM-22, ZSM-5, TNU-9, IM-512, e.g. ZSM-22 (TON like) or SAPO-34, SAPO-11, SAPO-44, ZSM-22 and ZSM-12, e.g. ZSM-2 (MTW like).

More preferred catalysts include ZSM-5 and MCM-22 zeolites with at least one active metal preferably selected from Mo, W, Zn, Re, Fe, V or Cr. The catalyst may be grown or treated in various ways, such as forming of hierarchical pore structures, deactivation of excess acid sites, addition of binders, and the addition of promoter metals (or other substances such as carbides). Research and development activities on potential new catalysts, and catalyst improvements, are ongoing at many academic and industrial groups, and the present invention may take advantage of any improvements in catalysts made in the future.

Highly preferred zeolites are ZSM-5 zeolites, especially HZSM-5 zeolites, where the metal may be Mo, W, Fe, V or Cr, listed starting with highest activity. Ga may also be used.

For methane dehydrogenation, the most preferred catalyst is a H-ZSM5 with an active metal with reported activity in the order Mo>W>Ga>Fe>V>Cr to form aromatic products.

For ethane dehydrogenation any of the above mentioned catalysts for methane is applicable, but preferred catalysts include alumina supported $Ga_2O_3$, $CrO_2$, $MoO_3$ and $V_2O_5$ such as $CrO_2$, $MoO_3$ and $V_2O_5$.

The choice of metal depends on the design, the desired activity and the compatibility with the membrane reactor.

In one embodiment the catalyst will be deposited on the membrane. This will be achieved by techniques such as dip coating or impregnation, where the catalyst is dispersed in a solution. The membrane is then heat treated so that the catalyst is adhered to the membrane surface. The deposition can also be achieved by growing the catalyst directly on the membrane by a crystal growth technique.

A second embodiment includes a reactor where the catalyst is freely lying on top of, or in front of the membrane. The catalyst can be in the form of powder with tailored particle size. The catalyst is not adhered to the membrane. In this embodiment the catalyst can therefore easily be exchanged if it needs to be regenerated.

Catalytic Membrane Reactor

In principle any reactor design can be used, however preferred reactor designs are flow-type fixed bed, fluidized bed and wash-coated designs. It is important therefore that there is flow from inlet to outlet in the first zone of the reactor. One advantageous design utilises a reactor within which there is a tubular transport membrane. Between the reactor walls and the tubular membrane is a bed of dehydrogenation catalyst. This forms the first zone in the reactor. This bed need not extend the whole length of the reactor but it may.

Hydrogen and alkane gases are fed into the space between the walls and membrane, i.e. into the first zone. Dehydrogenation and aromatisation occurs on contact between the reactants and the catalyst thus forming aromatic hydrocarbons and hydrogen. Hydrogen gas generated passes through the membrane and into the central part of the tubular membrane (the second zone) where that hydrogen can be removed to create a gradient for transport. This can be done using a sweep gas. Further this sweep gas can comprise oxygen or a compound comprising oxygen such as water. If an oxygen species is present then some oxygen may transport from the permeate side to the reactor chamber with benefits as highlighted above.

Current can also be applied as explained above to encourage transport of hydrogen across the membrane. Gases which pass through the catalyst bed and which do not pass through the membrane can be collected at the outlet in the first zone. A sweep gas can also be used in the case of electrical driven membrane.

It is preferred that the distance from the catalyst to the membrane is as short as possible, preferable no more than 5 cm and more preferable less than 5 mm.

It is preferred if hydrogen is removed in a counterflow direction to the flow of the reactant gases. It is important that the product gas is kept above 220° C. to avoid condensation of any aromatics such as naphthalene in the gas lines.

The aromatic compounds, hydrogen and unreacted alkane starting materials which exit the reactor need to be separated. Several processes for aromatic extraction exist using principles of separation that may include distillation, adsorption, membrane separation, chemical looping and pressure swing adsorption.

For example separation may be done by absorption of aromatics in liquid hydrocarbons, such as a 1-methyl-naphthalene absorber, followed by distillation to separate aromatics from the absorber.

Separation of these components can essentially be carried out using known conventional techniques.

Recycle

Once separated, the residual alkane and hydrogen can be disposed of but more preferably these are recycled to the start of the process. One embodiment of the invention further provides a process for recycling the unreacted alkanes back into the reactor or recycling hydrogen or more preferably recycling both hydrogen and alkanes back into the reactor thus avoiding the need for external hydrogen separation. In this embodiment, the product gas stream, which in addition to aromatic products also will at least contain unreacted alkanes such as methane as well as hydrogen, is sent to a separator (such as for example a distiller or an absorber) to extract aromatic products before at least a part of the unreacted alkane along with the hydrogen in the product gas is recycled back into the reactor inlet. Depending on the amount of hydrogen desired in the feed and the amount of hydrogen in the outlet gases it will be appreciated that fresh fed hydrogen may be needed or some hydrogen might need to be removed from the outlet gases to ensure that the right amount of hydrogen is fed to the reactor.

Thus, it is also an objective of the present invention to facilitate the energy efficient and economical integration of a recycle loop for unreacted gases to optimize the efficiency and economics of the total reactor system.

The recycled materials may be feed via their own dedicated line into the reactor or may be mixed with fresh feed materials into the reactor via the main reactor inlet. The skilled person will be able to devise a suitable recycling system.

It is generally preferred if the hydrogen content of the recycle stream is 3 to 35 vol %, preferably 7 to 30 vol %, such as 10 to 25 vol %. A most preferred range may be 10 to 20 vol %. It should be more than 3 mol %.

The invention will now be defined with reference to the following non limiting examples and figures.

BRIEF DESCRIPTION OF THE DRAWINGS

FIG. 1 is a flow diagram showing an outline of a process according to the present invention. Alkanes (A) and hydrogen are fed via inlet (4) into fluidised or fixed bed reactor (1) containing a dehydrogenation catalyst bed (5). Hydrogen passes through tubular transport membrane (2) leaving formed aromatic compounds (B), unreacted hydrogen and starting material exiting at outlet (3). Components A, B and hydrogen are separated in separating apparatus (6) and component A and hydrogen recycled via line (7) back to the initial feedstock. Component (B) is taken for optional further purification and use.

EXAMPLE 1

Membrane Preparation

A tubular asymmetric membrane of 65 wt. % NiBaZr$_{0.7}$Ce$_{0.2}$Y$_{0.1}$O$_{3-\delta}$ (BZCY72) support with a 30 μm dense membrane was synthesized using a reactive sintering approach (Coors et al. Journal of Membrane Science 376 (2011) 50-55). Precursors of BaSO$_4$, ZrO$_2$, Y$_2$O$_3$ and CeO$_2$ was mixed in stoichiometric amounts (metal basis) together with 1 wt. % NiO in a Nalgene bottle on a jar roller for 24 h. The material was dried in air and sieved through a 40 mesh screen. A portion of the mix was mixed additionally with 64 wt. % NiO and blended with water soluble acrylic and cellulosic ether plasticizer to prepare the extrusion batch. Green tubes were extruded using a Loomis extruder.

The extruded tubes were then dried and spray coated with the mixture with a 1 wt. % NiO solution. The tubes was the co-fired by hang-firing in air at 1500° C. for 4 h. The sintered tubes were then treated in a hydrogen mixture (safe gas) at 1000° C. to reduce the NiO to Ni and give the necessary porosity in support structure. Dimensions of the half-cell tube are ~25 cm long with an outer diameter of ~10 mm, an inner diameter of ~9.8 and a membrane thickness of ~30 μm.

A second outer electrode was prepared by mixing 50 vol. % of Cu-metal in BCZY72 pre-calcined powder. An ink was prepared using polyvinylpyrrolidine (PVP) and 50 vol. % ethylene glycol in isopropanol and coated on the reduced tube using a brush. The electrode was fired under reducing conditions (5% $H_2$ in Ar) at 1000° C. for 2 h. A Cu wire was used as current wires for the outer electrode and Pt wire for current wires for the inner electrode.

Catalyst Preparation

EXAMPLE 2

A commercial ZSM-5 powder was acquired by Zeolyst, batch CBV 2314 with a product number 2493-39. The catalyst was supplied in ammonia form ($NH_4$-ZSM-5) with a nominal $SiO_2/Al_2O_3$ ratio of 23. The catalyst is converted to the protonated form, H-ZSM-5 by calcination in air at 550° C. for 6 hours. Mo was introduced into the catalyst by incipient wetness impregnation using a solution of ammonium heptamolybdate tetrahydrate $(NH_4)_6Mo_7O_{24}\cdot 4H_2O$ in water, drying at 100° C. over night and then calcined at 500° C. for 18 h. Prior to catalytic membrane reactor testing the impregnated catalyst was pressed to pellets, crushed in a mortar and sieved to 250-420 μm to yield a suitable particle size for the reactor dimensions.

EXAMPLE 3

An MCM-22 zeolite was synthesized using hexamethylenimine as a template with a nominal $SiO_2/Al_2O_3$ ratio of 30. The catalyst was converted to the protonated form, H-MCM-22, by ion-exchange with 0.1M $NH_4NO_3$ and following calcination in air at 550° C. for 6 hours. Mo/H-MCM-22 catalyst was prepared as described in Example 2.

Reactor

Figure 4:
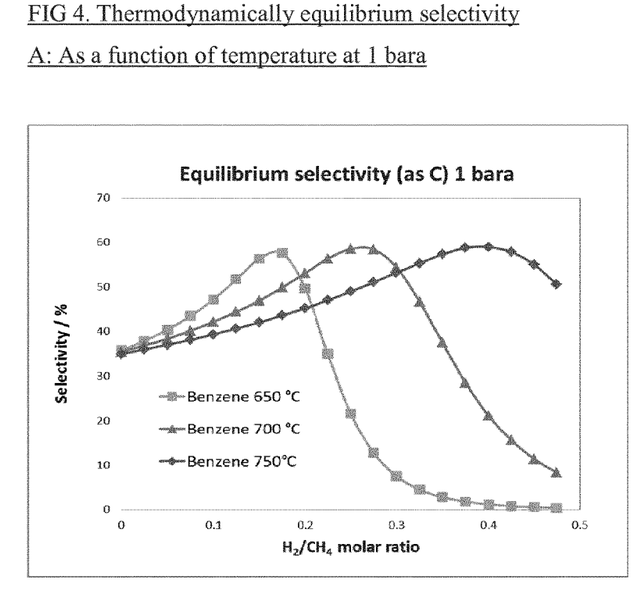
FIG. 4 shows thermodynamic equilibrium selectivity to benzene relative to other C1-C10 hydrocarbons for the dehydroaromatization of methane at different hydrogen to methane ratios at temperatures 650° C., 700° C. and 750° C. at pressures 1 and 3 bara at 700° C.
Figure 4B:
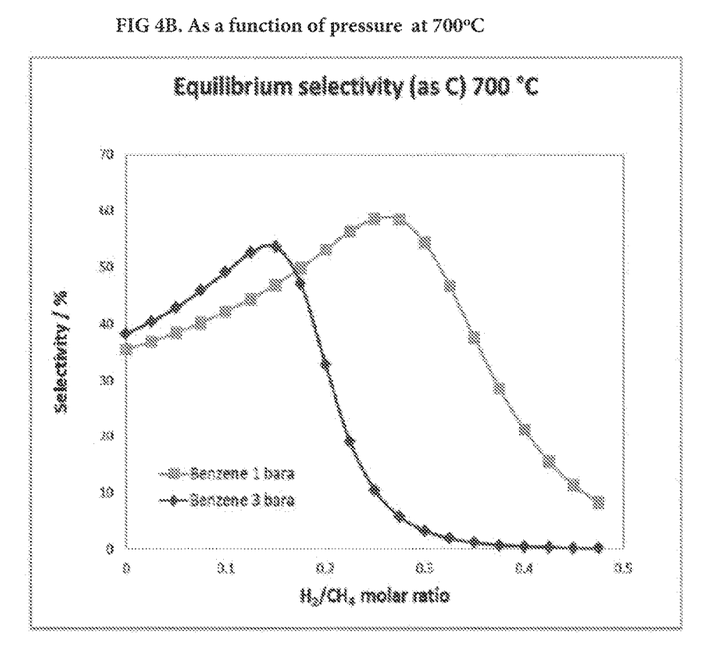

A fixed bed type reactor is utilized where the BZCY membrane is located in the centre of the fixed bed with the catalyst placed around the membrane. A sketch of the reactor is given in FIG. 4. The volume of the bed is given by the distance between the tube and the fixed bed wall. The feed flow is directed upwards through the catalyst bed along the membrane. An alumina single bore tube is placed on the inside of the membrane tube to supply sweep gas to the top of tube so that there is an even flow of sweep gas to the reactor inner tube outlet. A 3-zone furnace is used to have a uniform heat distribution of the active reactor length. It is important that the product gas is kept above 220° C. to avoid condensation of naphthalene in the gas lines.

Process

The reactor was operated at 700° C. using the reactor and membrane electrode assembly as described above. In total 2 g of 6 wt % Mo impregnated ZSM-5 catalyst was used in the experiment. The active area of the tube was 12.5 $cm^2$ and the catalyst was diluted with SiC to ensure that the catalyst covered the whole active area. The Cu and Pt wires, forming the outer and inner electrodes respectively, were connected to a Gamry Reference 3000 Potentiostate/Galvanostat/ZRA utilized in galvanostatic mode. Carboratization of the catalyst was done in-situ after heating in Ar with ~1% $H_2$ to 700° C. and then switching to $CH_4$. During operation the GHSV (gas hourly space velocity) was held at 1800 mL/h g, which yields a $CH_4$ flow of 60 mL/min. To simulate different hydrogen content in the gas feed a mass flow controller was utilized. For the sweep side a humidified (3% $H_2O$) 5% $H_2$ in Ar mixture was used with a flow of 50 mL/min. Both the product and the sweep side was monitored using a Agilent 7890B GC equipped with 2 MolSieve, 2 porapak and a HP-plot-q column and using a FID and TCD detector for the product stream and a TCD detector for the sweep stream. This enables quantification of the hydrogen and hydrocarbon content in the product stream and the hydrogen content in the sweep stream.

In table 1 the hydrogen concentration for the feed, sweep exhaust and product exhaust is given. In addition the benzene yield is presented.

TABLE 1

Hydrogen concentration in feed, sweep exhaust and product exhaust and aromatics yield in an experiment with GHSV of 1800 mL/gh at 700° C. at 1 bara.

| Feed $H_2$ mL/min | Sweep exhaust $H_2$ mL/min | Product exhaust $H_2$ mL/min | Aromatics yield/% | Benzene selectivity/% |
|---|---|---|---|---|
| 7 | 1.63 | 9.55 | 2.72 | 68 |
| 9 | 1.56 | 10.44 | 2.40 | 69 |
| 11 | 1.17 | 11.25 | 1.43 | 70 |
| 12 | 1.10 | 10.62 | 1.59 | 70 |

Results given in table 1 shows that with in-situ hydrogen removal it is possible to adjust the hydrogen concentration in the product exhaust. This can be made lower or the same as the feed hydrogen concentration. Coke formation decreases and catalyst lifetime increases, with increasing hydrogen partial pressure as expected from thermodynamic calculations. It is also shown that the aromatic yield decreases with increasing hydrogen feed, which implies a decrease in the overall conversion due to the shift in the equilibrium towards methane. It can also be seen that the selectivity towards benzene increases with increasing hydrogen feed, again as expected from thermodynamic calculations given in FIG. 5.

The preferred operation principle is dependent on the overall process. If the goal is to achieve high yield, low hydrogen feed and/or a high level of hydrogen extraction across the hydrogen transport membrane is favoured. If the process is continuous and includes an efficient recycling loop the co-feed should be adjusted to optimize total process economics, taking into account also the cost/value balance of the recycle gas. It must be appreciated that this laboratory example is not optimised and on larger scale yields would be expected to be higher as more hydrogen can be removed via the membrane.

The following examples are based on the protocols above varied as described in each example:

EXAMPLE 4

A process operated at 700° C., 1500 mL/h g and 1 bara using simulated recycle feed of 5 vol % $H_2$, Mo impregnated ZSM-5 zeolite and membrane electrode assembly as described above.

EXAMPLE 5

A process operated at 700° C., 1500 mL/h g and 1 bara using simulated recycle feed of 10 vol % $H_2$, Mo impregnated ZSM-5 zeolite and membrane electrode assembly as described above.

EXAMPLE 6

A process operated at 700° C., 1500 mL/h g and 1 bara using simulated recycle feed of 15 vol % $H_2$, Mo impregnated ZSM-5 zeolite and membrane electrode assembly as described above.

EXAMPLE 7

A process operated at 700° C., 1500 mL/h g and 1 bara using simulated recycle feed of 5 vol % $H_2$, Mo impregnated MCM-22 zeolite and membrane electrode assembly as described above.

EXAMPLE 8

A process operated at 700° C., 1500 mL/h g and 1 bara using simulated recycle feed of 10 vol % $H_2$, Mo impregnated MCM-22 zeolite and membrane electrode assembly as described above.

TABLE 3

Feed composition and products formation rate in nmol/g s from Examples 4 to 8 after 3 h on stream.

| | Feed | | Product exhaust | | | |
|---|---|---|---|---|---|---|
| | | | | Alkanes | | |
| Example | $H_2$/ nmol/g s | $CH_4$/ nmol/g s | $H_2$/ nmol/g s | (C1-C2)/ nmol/g s | Benzene/ nmol/g s | Coke/ nmol/g s |
| 4 | 845 | 16380 | 2751 | 13642 | 900 | 600 |
| 5 | 1704 | 20108 | 3170 | 17497 | 557 | 1022 |
| 6 | 2535 | 20108 | 3604 | 18583 | 320 | 981 |
| 7 | 845 | 16380 | 2234 | 15556 | 1174 | 445 |
| 8 | 1704 | 20108 | 2241 | 16234 | 1075 | 357 |

TABLE 4

Products formation rate in nmol/g s from Example 8 with and without hydrogen removal.

| | Without hydrogen removal | With hydrogen removal |
|---|---|---|
| CO [nmol $g^{-1}$ $s^{-1}$] | 0 | 63 |
| Benzene [nmol $g^{-1}$ $s^{-1}$] | 810 | 1075 |
| Coke [nmol $g^{-1}$ $s^{-1}$] | 398 | 357 |

EXAMPLE 9

Figure 5:
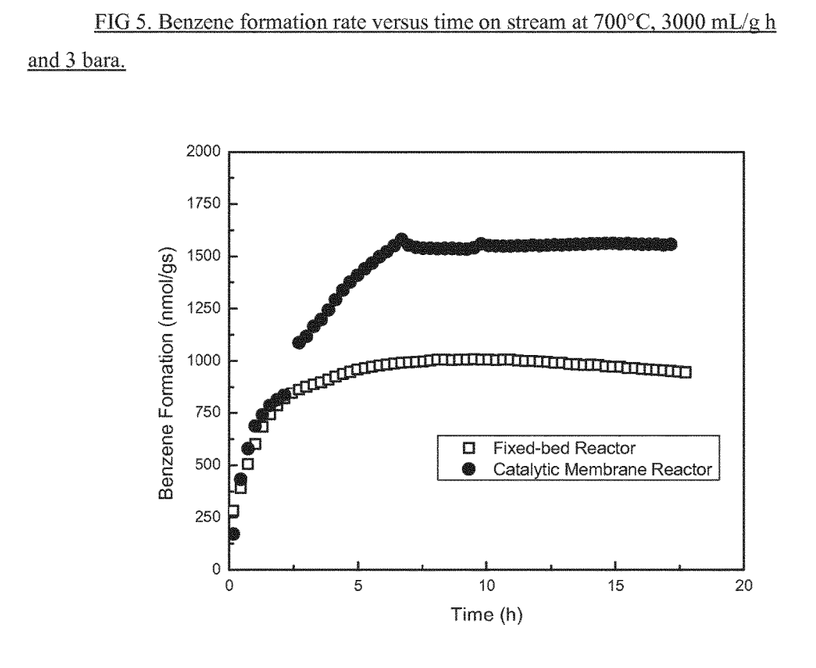
FIG. 5 shows the formation rate of benzene versus time on stream at 700° C., 3000 mL/g h and 3 bara in a catalytic membrane reactor and a conventional fixed-bed reactor.

A process operated at 700° C., 3000 mL/h g and 3 bara using simulated recycle feed of 5 vol % $H_2$, Mo impregnated MCM-22 zeolite and membrane electrode assembly as described above. FIG. 5 shows the benzene formation rate in nmol/s g versus time on stream for this process (catalytic membrane reactor). It is also included for comparison the obtained benzene formation in a conventional fixed-bed reactor without hydrogen removal.

EXAMPLE 10

A process operated at 725° C., 3000 mL/h g and 1 bara using simulated recycle feed of 5 vol % $H_2$, Mo impregnated MCM-22 zeolite and membrane electrode assembly as described above.

EXAMPLE 11

A process operated at 725° C., 3000 mL/h g and 3 bara using simulated recycle feed of 5 vol % $H_2$, Mo impregnated MCM-22 zeolite and membrane electrode assembly as described above.

TABLE 5

Feed composition and products formation rate in nmol/g s from Examples 9 to 11 after 6 h on stream.

| | Feed | | Product exhaust | | | |
|---|---|---|---|---|---|---|
| | | | | Alkanes | | |
| Ex | $H_2$/ nmol/g s | $CH_4$/ nmol/g s | $H_2$/ nmol/g s | (C1-C2)/ nmol/g s | Benzene/ nmol/g s | Coke/ nmol/g s |
| 9 | 1745 | 32950 | 3287 | 27409 | 1552 | 1167 |
| 10 | 1745 | 32950 | 4406 | 32391 | 1540 | 924 |
| 11 | 1745 | 32950 | 4385 | 27290 | 1588 | 1025 |

EXAMPLE 12

A process operated at 700° C., 1500 mL/h g and 1 bara with Mo impregnated MCM-22 zeolite and membrane electrode assembly as described above.

TABLE 6

Rate of formation of benzene and hydrogen removal in an experiment with GHSV of 1500 mL/gh at 700° C. and 1 bara while using wet and dry sweep during hydrogen removal.

| | Without hydrogen removal | With hydrogen removal | |
|---|---|---|---|
| | | Dry sweep | Wet sweep |
| Benzene [nmol $g^{-1}$ $s^{-1}$] | 850 | 1027 | 1174 |
| Hydrogen removal [nmol $g^{-1}$ $s^{-1}$] | 0 | 136 | 1226 |

The invention claimed is:

1. A process for the preparation of an aromatic hydrocarbon in a catalytic membrane reactor comprising a reactor inlet, a dehydrogenation catalyst and a reactor outlet in a first zone arranged so that a feed to the reactor via the inlet must contact the dehydrogenation catalyst before passing to the reactor outlet;
and a hydrogen transport membrane separating said first zone from a second zone; said process comprising:
(I) feeding through said reactor inlet a feed comprising hydrogen and at least one C1-4 alkane so that the alkane and hydrogen contact said dehydrogenation catalyst in said first zone;
(II) operating said reactor at a temperature and pressure sufficient to allow dehydrogenation of said alkane and formation of said aromatic hydrocarbon and hydrogen;

(III) allowing hydrogen to selectively pass through the hydrogen transport membrane into said second zone;

(IV) recovering through the reactor outlet in the first zone, said aromatic hydrocarbon along with any unreacted C1-4 alkane and any hydrogen not extracted through the hydrogen transport membrane;

(V) separating the aromatic hydrocarbon from the hydrogen and any unreacted C1-4 alkane; and (VI) recycling at least a part of said hydrogen and any unreacted C1-4 alkane to the feed using a recycle stream, wherein the hydrogen content of the recycle stream is 3 to 35 vol %.

2. The process of claim 1, wherein hydrogen transfer through said membrane take place in the form of protons.

3. The process of claim 2, wherein a partial pressure of hydrogen in the second zone of the catalytic membrane reactor is maintained at a low level by sweeping with an oxygen containing gas to convert at least some of the hydrogen to water in the second zone.

4. The process of claim 1, wherein the ratio of hydrogen to alkanes on a molar basis is higher at a feed side than at a product side of the catalytic membrane reactor.

5. The process of claim 1, wherein the ratio of hydrogen to alkanes on a molar basis is the same at a feed side and at a product side of the catalytic membrane reactor.

6. The process of claim 1, wherein an electrochemical driving force for the hydrogen transport across the hydrogen transport membrane is the result of an external voltage being applied to the membrane.

7. The process of claim 1, wherein an electrochemical driving force for the hydrogen transport across the hydrogen transport membrane is the result of a difference in partial pressures of hydrogen on the two sides of the membrane.

8. The process of claim 1, wherein said dehydrogenation catalyst is a zeolite catalyst.

9. The process of claim 8, wherein said zeolite has the structure MWW, CHA or WI.

10. The process of claim 9, wherein said zeolite is a ZSM-5.

11. The process of claim 1, wherein said transport membrane comprises at least one mixed metal oxide of formula (II)

$$Ln_a W_{b-c} Mo_c O_{12-y} \qquad (II)$$

wherein Ln is Y or an element numbered 57 to 71; the molar ratio of a:b is 4.8 to 6; c is 0 to (0.5×b); and y is a number such that formula (II) is uncharged.

12. The process of claim 1, wherein the feed is natural gas.

13. The process of claim 1, wherein temperature in reactor is 500 to 1000° C.

14. The process of claim 1, wherein a portion of oxygen originating from an oxygen containing gas present in the second zone is transported from the second zone to the first zone.

15. A process for the preparation of an aromatic hydrocarbon in a catalytic membrane reactor comprising a reactor inlet, a dehydrogenation catalyst and a reactor outlet in a first zone arranged so that a feed to the reactor via the inlet must contact the dehydrogenation catalyst before passing to the reactor outlet;

and a hydrogen transport membrane separating said first zone from a second zone; said process comprising:

(I) feeding through said reactor inlet a feed comprising hydrogen and at least one C1-4 alkane so that the alkane and hydrogen contact said dehydrogenation catalyst in said first zone;

(II) operating said reactor at a temperature and pressure sufficient to allow dehydrogenation of said alkane and formation of said aromatic hydrocarbon and hydrogen;

(III) allowing hydrogen to selectively pass through the hydrogen transport membrane into said second zone;

(IV) removing hydrogen from said second zone in order to establish a concentration gradient for hydrogen transport between said first and second zones;

(V) recovering through the reactor outlet in the first zone, said aromatic hydrocarbon along with any unreacted C1-4 alkane and any hydrogen not extracted through the hydrogen transport membrane;

(VI) separating the aromatic hydrocarbon from the hydrogen and any unreacted C1-4 alkane; and (VII) recycling at least a part of said hydrogen and any unreacted C1-4 alkane to the feed using a recycle stream, wherein the hydrogen content of the recycle stream is 3 to 35 vol %.

16. The process of claim 15, wherein the step (IV) of removing hydrogen from said second zone in order to establish a concentration gradient for hydrogen transport between said first and second zones is achieved by sweeping with an oxygen containing gas to convert at least some of the hydrogen to water.

17. The process of claim 16, wherein oxygen is derived from said oxygen containing gas.

* * * * *